United States Patent
Kanter et al.

(10) Patent No.: US 6,903,227 B2
(45) Date of Patent: Jun. 7, 2005

(54) SYNTHESIS OF 2-ACYL SUBSTITUTED CHROMANES AND INTERMEDIATES THEREOF

(75) Inventors: James Kanter, South San Francisco, CA (US); John J. G. Mullins, San Francisco, CA (US); Anjali Pandey, Fremont, CA (US); Robert Scarborough, Half Moon Bay, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 201 days.

(21) Appl. No.: 10/297,103

(22) PCT Filed: Jun. 1, 2001

(86) PCT No.: PCT/US01/17667

§ 371 (c)(1),
(2), (4) Date: May 6, 2003

(87) PCT Pub. No.: WO01/92250

PCT Pub. Date: Dec. 6, 2001

(65) Prior Publication Data

US 2003/0233002 A1 Dec. 18, 2003

Related U.S. Application Data

(60) Provisional application No. 60/208,588, filed on Jun. 2, 2000, and provisional application No. 60/208,764, filed on Jun. 2, 2000.

(51) Int. Cl.[7] .......................... C07D 311/58; C12P 17/06
(52) U.S. Cl. ....................................... 549/404; 435/125
(58) Field of Search ........................... 549/404; 435/125

(56) References Cited

U.S. PATENT DOCUMENTS 5,703,026 A 12/1997 Setser et al.
5,731,324 A 3/1998 Fisher et al.
6,756,403 B2 * 6/2004 Briggs et al. ................ 514/456
2004/0014804 A1 * 1/2004 Antoine et al. ............. 514/456
2004/0014994 A1 * 1/2004 Antoine et al. ............. 549/404

FOREIGN PATENT DOCUMENTS

DE 198 58 341 A1 6/2000
WO WO 00/35901 6/2000

OTHER PUBLICATIONS

R.E. Mewshaw, et al., "New Generation Dopaminergic Agents 4. Exploiting the 2–Methyl Chroman Scaffold. Synthesis and Evaluation of Two Novel Series of 2–(Aminomethyl)–3,4,7,9–tetrahydro–2H–pyrano [2,3–e] indole and Indol–8–one Derivatives," *Tetrahedron*, vol. 54, 1998, pp. 7081–7108, 1998.

R.E. Mewshaw, et al., "New Generation Dopaminergic Agents 1. Discovery of a Novel Scaffold Which Embraces the $D_2$ Agonist Pharmacophore. Structure—Activity Relationships of a Series of 2–(Aminomethyl) Chromans," *J. Med. Chem*, 1997, vol. 40, pp. 4235–4256.

* cited by examiner

*Primary Examiner*—Fiona T. Powers
(74) *Attorney, Agent, or Firm*—Knobbe, Martens, Olson & Bear, LLP

(57) ABSTRACT

Novel processes for producing enantiomerically enriched and enantiomerically pure compositions of 2-acyl substituted chromane compounds, and 2-acylchromane compounds that are intermediates for producing platelet aggregation inhibitors and/or are themselves potent platelet aggregation inhibitors are disclosed. Further disclosed are processes for producing salts such as acid addition salts for such enantiomerically enriched compositions.

45 Claims, No Drawings

SYNTHESIS OF 2-ACYL SUBSTITUTED CHROMANES AND INTERMEDIATES THEREOF

This is the U.S. national phase under 35 U.S.C. §371 of International application PCT/US01/17667, published in English, filed Jun. 1, 2001, which claims priority to U.S. Provisional Application Nos. 60/208,588, filed Jun. 2, 2000; and 60/208,764, filed Jun. 2, 2000.

FIELD OF THE INVENTION

This invention relates to novel processes for producing enantiomerically enriched and substantially enantiomerically pure compositions of 2-acyl substituted chromane compounds, and 2-acylchromane compounds that are intermediates for producing platelet aggregation inhibitors and/or are themselves potent platelet aggregation inhibitors. Further, the invention relates to processes for producing salts such as acid addition salts for such enantiomerically enriched compositions.

BACKGROUND OF THE INVENTION

The production of 2-acyl-4-oxo-chromenes (2-acylchromones) by ring closure or substituted benzene ring structures are well known in the art. One known initial process step for the production of 4-oxochromene-2-carboxylic acid, or derivatives of such acids including acid halides or esters, uses 2-hydroxy-acetophenone compounds as starting materials. (See e.g., J. Med. Chem., Vol. 15, No. 8, 1972.) The reaction scheme to produce the 2-carboxylic acid and esters is as follows:

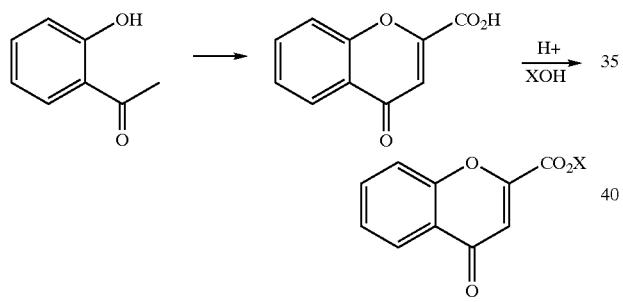

where X is ethyl, for example. The acid can be converted to an acyl halide, such as acyl chloride, instead of the ethyl ester by reacting it with $SOCl_2$, for example. A further reaction of the acyl chloride with $NH_3$ can be used to produce the carboxamide.

The above chromene-derivative compounds have been reported as useful intermediates for the production of compounds wherein the phenyl ring of the chromene ring structure is further substituted by a benzoylamino derivative to produce antidepressants. See, for example, U.S. Pat. No. 5,659,051.

One synthesis of racemic 2-(chroman4-one-2-yl)acetic acid derivatives begins with treating a coumarin derivative with a reducing agent such as diisoamylborane, lithium tri-butoxyaluminohydride, lithium triethylborohydride, lithium trimethoxyaluminium hydride, sodium borohydride, $H_2$/Pd/C, or the like. The reagent and reaction conditions may be selected to reduce either the α,β-double bond to the alkane, or the lactone to a lactol, or both. In a preferred aspect of the invention, lithium tri-butoxyaluminohydride, $LiAlH_4$ is used to reduce the lactone at the 2-position to a lactol.

The lactol hydroxyl group may be converted into a carboxymethyl group by standard chain extension/replacement reactions. For example, treating the lactol with chloroacetate under basic conditions, for example in the presence of pyridine, results in a carboxymethyl group at the 2-position.

SUMMARY OF THE INVENTION

The present invention relates to novel processes for producing enantiomerically enriched or substantially enantiomerically pure compositions of 2-chromanylcarboxylic acid compounds and 2-chromanylacetic acid esters, which are intermediates for producing therapeutic agents, or are themselves therapeutic agents for disease states in mammals that have disorders caused by or impacted by platelet dependent narrowing of the blood supply.

In accordance with a preferred embodiment, there is provided a process for making a compound according to the formula

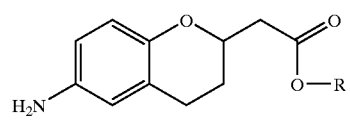

wherein R is H or an alkyl group. The process comprises (a) through (f):

(a) hydrogenating a compound of the formula:

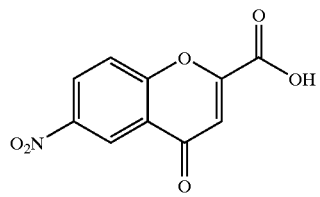

to produce a compound of the formula:

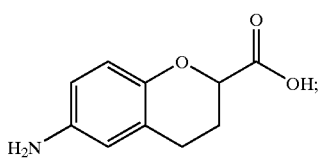

(b) reducing the carboxylic acid of compound of (a) to afford a compound as follows:

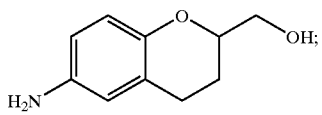

(c) transforming the hydroxyl group of compound of (b) into a leaving group to afford a compound as follows:

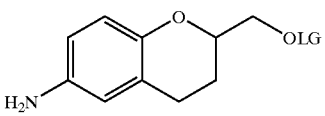

wherein OLG is a leaving group attached to oxygen;

(d) reacting the compound of (c) with cyanide ion to afford a compound as follows:

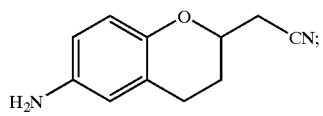

(e) hydrolyzing the compound of (d) to afford a compound as follows:

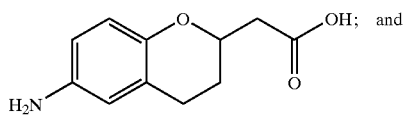

(f) optionally adding an alkyl group to form an ester.

In preferred embodiments, the hydrogenation of (a) is performed with H₂/Pd/C, and/or the reduction of (b) is performed with a chemical reducing agent, preferably lithium aluminum hydride, borane, or aluminum hydride.

In preferred embodiments the OLG of (c) is tosylate, mesylate, or halogen, and/or the hydrolysis (e) is performed with heating the compound made in (d) in aqueous mineral acid, preferably hydrochloric acid.

In one preferred embodiment, (e) and (f) are performed in one reaction mixture containing reagents comprising a mineral acid and an alcohol. Preferably the mineral acid is hydrochloric acid and the alcohol is ethanol.

In accordance with another preferred embodiment, there is provided a process for making a compound according to the formula

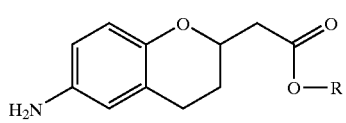

wherein R is H or an alkyl group. The process comprises (a) through (e):

(a) halogenating a compound of the formula:

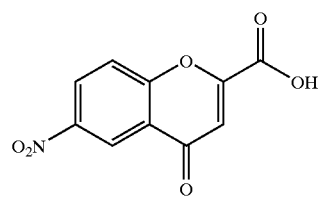

to produce a 2-hydroxy chromane compound of the formula:

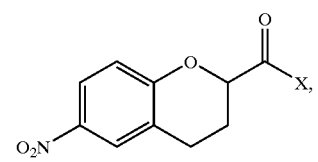

wherein X is a halogen;

(b) reacting the compound of (a) with cyanide ion to afford a compound as follows:

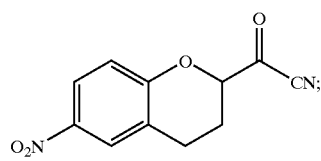

(c) hydrolyzing the compound of (b) to afford a compound as follows:

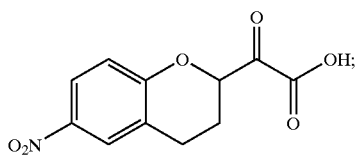

(d) reducing the keto group and nitro groups of compound of (c) by hydrogenation to afford a compound as follows:

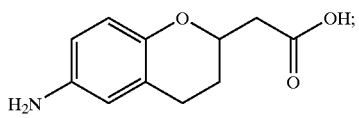

(e) optionally adding an alkyl group to form an ester.

In a preferred embodiment, the halogenation (a) is performed with thionyl chloride, thereby producing a compound of the formula:

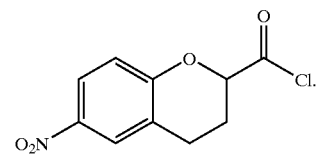

In preferred embodiments, the hydrolysis (c) is performed with heating the compound formed in (h) in aqueous mineral acid, preferably hydrochloric acid, the hydrogenation of step (d) is performed with H₂/Pd/C, and/or the esterification step (e) is performed with a mineral acid and an alcohol, preferably hydrochloric acid and ethanol.

In accordance with another preferred embodiment, there is provided a process for making a compound according to the formula

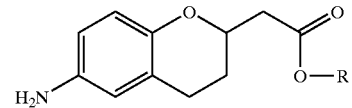

wherein R is H or an alkyl group. The process comprises (a) through (f):

(a) hydrogenating a compound of the formula and adding a protecting group to a subsequently formed amine:

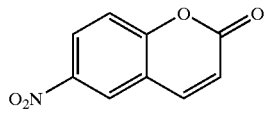

to produce a compound of the formula:

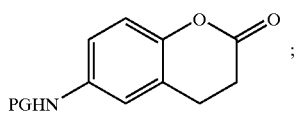;

(b) reducing the ketone of the lactone of compound of (a) to afford a compound as follows:

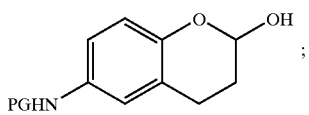;

(c) transforming the hydroxyl group of compound of (b) into a carbon chain with a carbon nucleophile to afford a compound as follows:

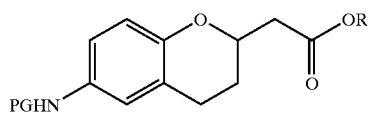

wherein R is an alkyl group;

(d) hydrolyzing the compound of (c) to remove the alkyl group from the ester to afford a compound as follows:

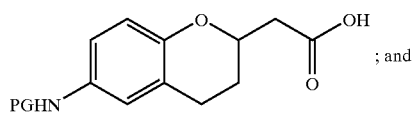; and (e) removing the protecting group from the amine, thereby obtaining the compound of the formula:

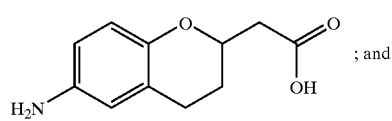; and (f) optionally adding an alkyl group to form an ester.

In a preferred embodiment, the hydrogenation (a) is performed with $H_2/Pd/C$, the reduction (b) is performed with chemical reducing agents preferably DIBAL-H, the carbon nucleophile of (c) is a phosphorus ylide preferably (carbethoxymethylene) triphenyl-phosphine, and/or PG is t-BOC or acetyl.

In preferred embodiments, the foregoing processes make a compound according to the formula:

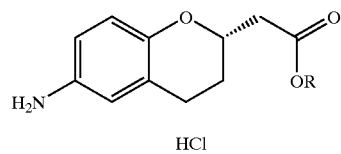

in greater than 95% enantiomeric purity with respect to the corresponding (2R) enantiomer, by one of the foregoing processes further comprising:

(i) resolving the racemate; and
(ii) forming the hydrochloride salt of the resolved amine compound.

In accordance with another preferred embodiment, there is provided a process for making a compound according to the formula

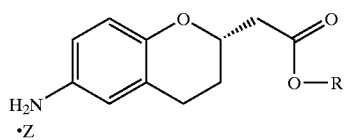

wherein R is an alkyl group and Z is a counterion to the amine salt. The process comprises:

(a) hydrogenating the compound of the formula:

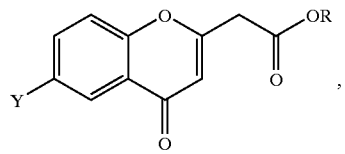, wherein Y is a nitro, amino or protected amino group, with a chiral catalyst to afford a compound as follows:

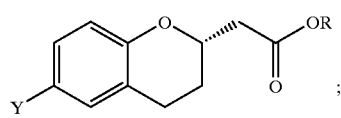;

(b) optionally reducing the nitro group of compound of (a) by hydrogenation to afford a compound as follows or removing the amino protecting group to produce a compound of the formula:

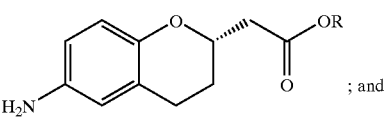; and (c) forming the amine salt by reaction of compound of (b) with a mineral acid.

In preferred embodiments, the chiral catalyst comprises ruthenium, rhodium, palladium or platinum.

DETAILED DESCRIPTION OF THE PREFERRED EMBODIMENTS

There is a need for improved processes for producing enantiomerically enriched or substantially enantiomerically pure compounds and intermediates for the synthesis of platelet aggregation inhibitors in which the benzene ring of the benzopyran is substituted differently than for the antidepressants reported in U.S. Pat. No. 5,659,051; and further, in which the 4-keto group is reduced to a methylene group, and the 2,3-double bond of the pyran is saturated. The procedures outlined above provide routes to these reduced species as chromane carboxylic acids. Thus, there is a need for an inexpensive, large-scale process for resolving these chiral benzopyran or chromane compounds into enantiomerically enriched or substantially enantiomerically pure compositions. Inherent losses of at least 50% of the starting material in any enantiomeric resolution require that the process be sufficiently efficient and inexpensive to be run on the industrial scale necessary to produce the large quantities of intermediate or final 2-chromanylacetic acid compounds needed for anticoagulant applications. A procedure that regenerates the racemate from the undesired enantiomer would improve the overall efficiency of the resolution process by allowing improved recoveries of the desired enantiomer.

One or more of the foregoing needs may be met using the processes described herein and the compounds and intermediates made thereby.

In particular, the present invention provides a process comprising a racemate resolution step as follows:

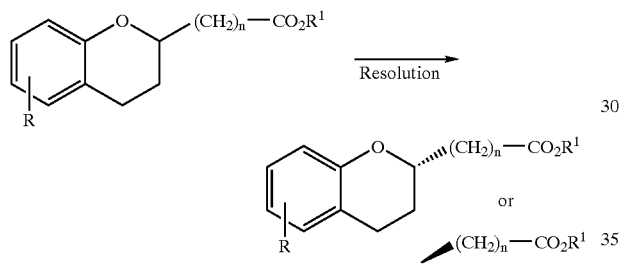

R is a substituent on the benzene ring such as amino, a protected amino group such as benzamido or acetamido, or a group that can be converted to an amino group (e.g., hydrogen or halogen). $R^1$ is hydrogen or alkyl group. Preferably, the 2-carboxylic acid group is esterified with a methyl or ethyl group and the R group on the benzene portion is nitro, amino, or protected amino. More preferably, R is an acyl protected amino group, e.g., acetamido or benzamido.

In a preferred aspect of this invention, the amino group is at the 6-position of the benzene ring and is protected, for example as acetamido. We have discovered that alaninol and racemic chromane carboxylic acids form diastereomeric salts that are unexpectedly easy to separate. When D-alaninol is used, S-chromane salts are recovered as crystals from methanol; when L-alaninol is used, R-chromane salts are recovered as crystals from methanol. Alternatively, when D-alaninol is used, R-chromanes are recovered from the supernatant. Likewise, when L-alaninol is used, S-chromanes are recovered from the supernatant. The yield is about 40–50% of 95% or greater purity of the desired, crude diastereomer. Essentially diastereomerically pure material can be obtained from the crude diastereomer by refluxing in methanol. Yields may be optimized by varying the amount of methanol used in this step.

Optionally, the amino group on the benzene ring of the compound can be deprotected after removing the alaninol, and the free acid esterified with an acidic alcohol solution. Also, a mineral acid salt such as the hydrochloride salt of the amino group may be formed by exposing the compound to the mineral acid such as hydrochloric acid, preferably in a one pot process at the end of the ester formation by increasing the mineral acid content.

Where the 2-hydroxyacetophenone starting material of the Allan-Robinson reaction does not contain a nitro or amino group, neither will chromone product of that reaction. This chromone (3) may be nitrated at the 6-position as shown:

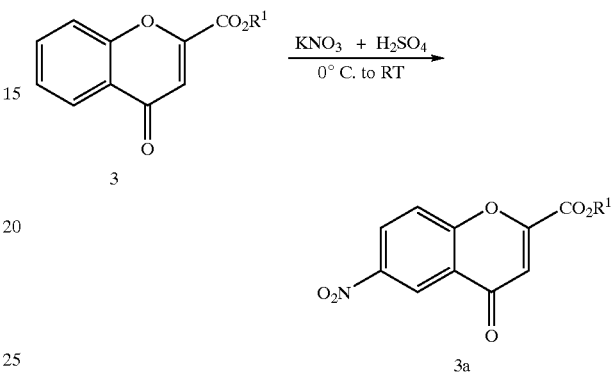

The major product is nitration at the 6-position as shown in product 3a. The nitro group may also be introduced by other means, such as brominating the chromone followed by substituting the bromine with nitro, for example. The direct nitration is preferred, however, as more straightforward.

Reducing the chromone (3 or 3a) 4-keto group and 2,3-double bond produces a chromane ring system, conditions under which the nitro group on the benzene ring may also be reduced to an amine. Standard reduction conditions, including catalytic hydrogenation and use of chemical reducing agents—for example, diisoamylborane, lithium tri-butoxyaluminohydride, $H_2/Pd/C$, and the like—may be used. In a preferred aspect, lithium tri-butoxyaluminohydride or $LiAlH_4$ also reduces the carboxylate ester at the 2-position to a hydroxymethyl group (compound 4).

An example of the conversion of the keto compound to the chromane core is as follows:

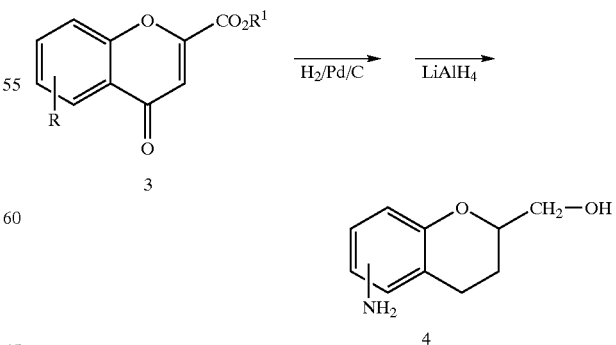

In this example, a nitro group in the starting material is reduced to an amino group, which is preferably in the 6-position on the chromane ring as shown:

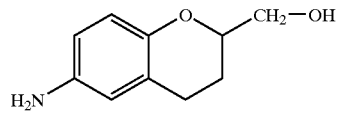
4

This compound may be further modified by converting the 2-hydroxymethyl into a chromanyl-substituted acetic acid or acetic acid ester, as follows:

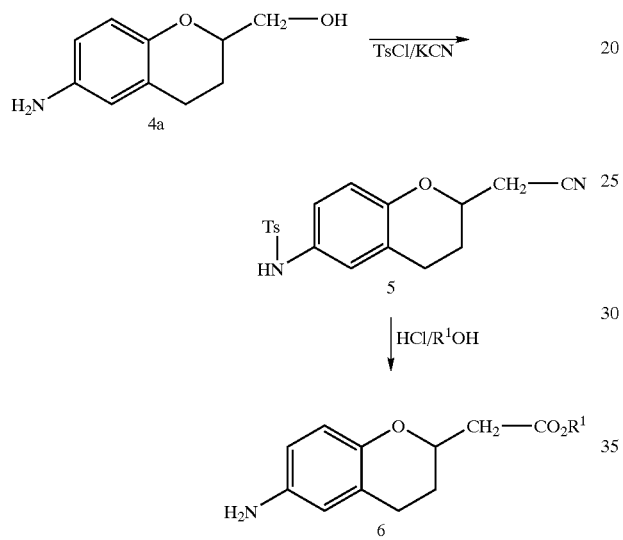

Here, R$^1$ is preferably an ethyl group. As shown above, the free amine may be tosylated in the step in which cyanide replaces hydroxyl. The tosyl group may be removed concomitant with the hydrolysis of the nitrile to the carboxylate with excess concentrated HCl. Alternatively, after nitrile hydrolysis, the hydrochloric acid may be removed from the reaction mixture—by neutralization of the solution and recrystallization of the product from isopropyl alcohol, for example—and a more nucleophilic acid such as hydrobromic acid may be used to hydrolyze the toluenesulfonamide. In such circumstances, care should be taken to avoid converting the carboxylic acid into an acyl bromide.

In an alternative embodiment of the present invention, compound 3 (above, acid or ester) may be converted first into an acyl halide, then the halide replaced with a cyano group to produce an α-ketonitrile, The α-ketonitrile may be hydrolyzed with a strong acid to form an α-ketocarboxylic acid, which may be catalytically hydrogenated in glacial acetic acid to produce chroman-2-ylacetate esters. This procedure avoids multiple hydrogenation steps or reducing the carboxyl group to hydroxymethyl before adding the nitrile. In a preferred aspect, the nitro group at the 6-position is retained until it is converted to an amino group during the hydrogenation step. In a further preferred aspect, compound 1 is 2-hydroxyacetophenone and the ester form of compound 3 is nitrated prior to conversion into the acyl halide. This procedure obviates the amine sulfonylation-desulfonylation reactions needed in the hydride reduction process.

In the following illustration, steps 1a and 2a show the conversion of compound 3 into an acyl halide (here, chloride) and the substitution of the halide by CN:

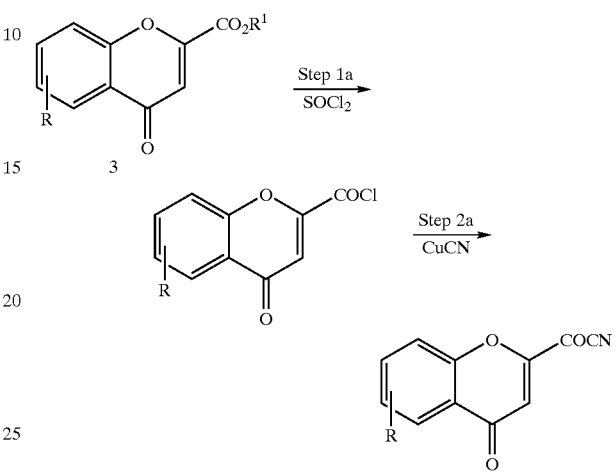

Preferably, the R group is nitro, which can later be reduced to amino. More preferably, the nitro is at the 6-position of the chromone. The α-ketonitrile at the 2-position is converted into an α-ketocarboxylic acid with a strong mineral acid, such as hydrochloric acid, as follows:

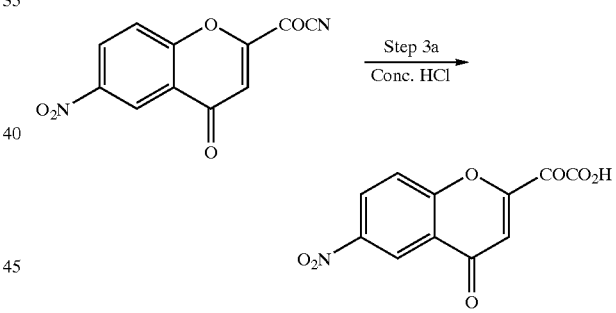

Preferably, the chromone keto group, the 2-keto substituent, the nitro group, and the 2,3-double bond are hydrogenated in a single step. However, in one embodiment, the hydrogenation is conducted in two steps. The first step is hydrogenation under mild conditions in the presence of an alcohol, such as methanol, ethanol, or the like; or in ethyl acetate or the like, at about 30 psi of hydrogen for about 1–2 h, followed by purging the apparatus with nitrogen, then hydrogen. In the second step, glacial acetic acid is added to the reaction mixture, the hydrogen pressure is increased to 45–65 psi, and the temperature raised to between 50–95° C. until the hydrogenation is complete. The progress of each of these reactions may be monitored by HPLC. While the hydrogenation may be viewed as either a one-step or two-step process, it is a one-pot procedure preferably requiring no separation step.

The procedure performed in a single hydrogenation step may be exemplified as follows:

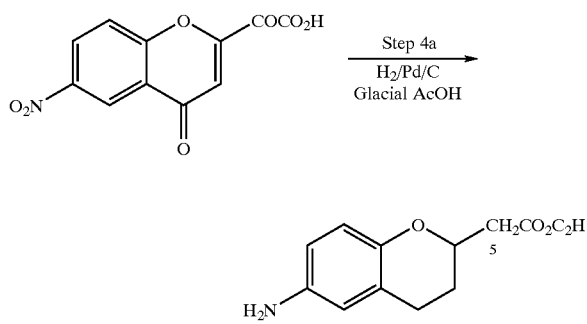

This procedure provides the racemic ethyl chroman-2-ylacetate compounds in good yield. These compounds may optionally be resolved as set forth below.

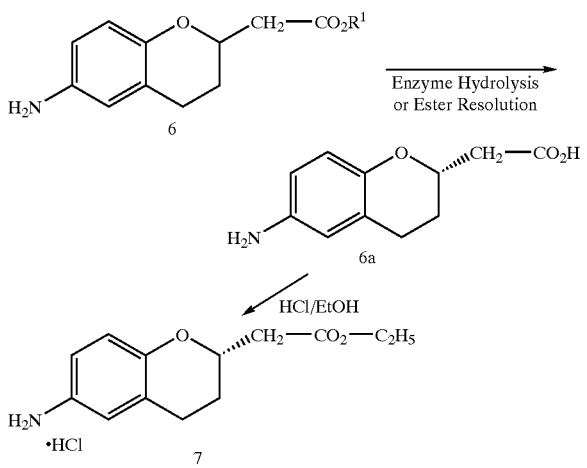

If desired, the chroman-2-ylacetate esters may be resolved through methods well known in the art. For example, the ester group may be modified with conventional resolving agents such as camphorsulfonic acid derivatives, dibenzoyl-tartaric acid derivatives, and the like. Alternatively, one enantiomer of the ester may selectively hydrolyzed enzymatically. The amino group may be oxidized to a nitro group whose electron-withdrawing character aids the hydrolysis reaction, or the resolution step may be done prior to reducing the nitro group to an amine as shown above.

In this example, the ethyl ester of the S-enantiomer is the product of the reesterification of the resolved carboxylic acid; however, other esters, such as the methyl or propyl, may likewise be envisioned. Hydrochloric acid in the reesterification step also converts the amine to its hydrochloride salt. In general, where the desired enantiomer is obtained as the carboxylic acid, treatment with ethanol and an excess of hydrochloric acid produces the ethyl ester of the carboxylic acid and the hydrochloride salt of the amine. The preferred recrystallization solvent for the resolved compounds is methanol or isopropanol. In a preferred aspect, the efficiency of the enzymatic resolution is increased by converting the 6-amino group into a 6-nitro group prior to the resolution and reconverting it into an amino group afterwards.

In a preferred aspect of the invention, the undesired enantiomer is converted into the racemate through a process comprising at least one ring-opening and one ring-closing step. This regenerated racemate is resubjected to the resolution procedure, thereby increasing the overall yield of the desired enantiomer, and consequently, the overall efficiency of the resolution.

In the syntheses of these compounds, amine or carboxylic acid groups may be protected to prevent undesired reactions of that functional group. Examples of suitable protecting groups are well known in the art. Furthermore, methods for removing these protecting groups, for example by hydrolysis or hydrogenolysis, are well known in the art.

Some non-limiting, exemplary synthetic schemes, each of which is a preferred embodiment of the invention, comprise the process steps outlined below. These synthetic schemes may include additional steps precedent, such as those set forth in *J. Med. Chem.*, Vol. 15, No. 8 (1972), or steps subsequent, for example converting the amine group into a different group, such as one affecting anticoagulant activity. Such modifications are advantageously effected through amine coupling reactions, which are well known in the art. The specific steps set forth in the schemes below are described in the Examples. In general, the reaction products are isolated and purified by conventional methods, typically by solvent extraction into a compatible solvent. Preferred solvents are lower alkane ethers and alcohols; ethyl ether and isopropyl alcohol are preferred for solvent extraction and recrystallization. L-alaninol is the preferred resolving agent since it is typically less expensive than D-alaninol, but other resolving agents or analogous procedures may be used. The products may be further purified by column chromatography or by other appropriate methods.

Scheme I

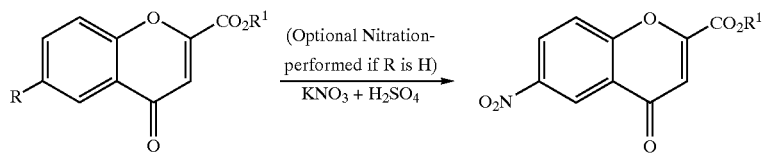

J. Med. Chem., Vol 15, No.8 (1972)
R = H, NO$_2$, NH$_2$ or Benzoylamino
R$^1$ = Me, Et or Pr

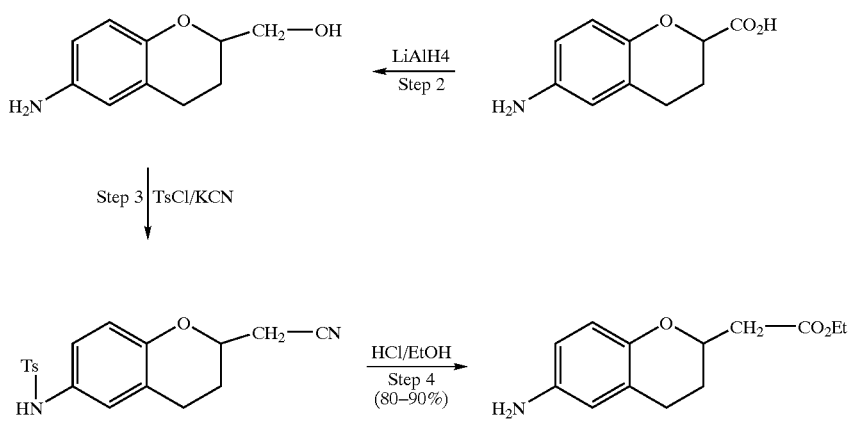
if a chiral catalyst is used in Step 1, desired stereochemistry at the 2-position can be achieved.
Scheme II
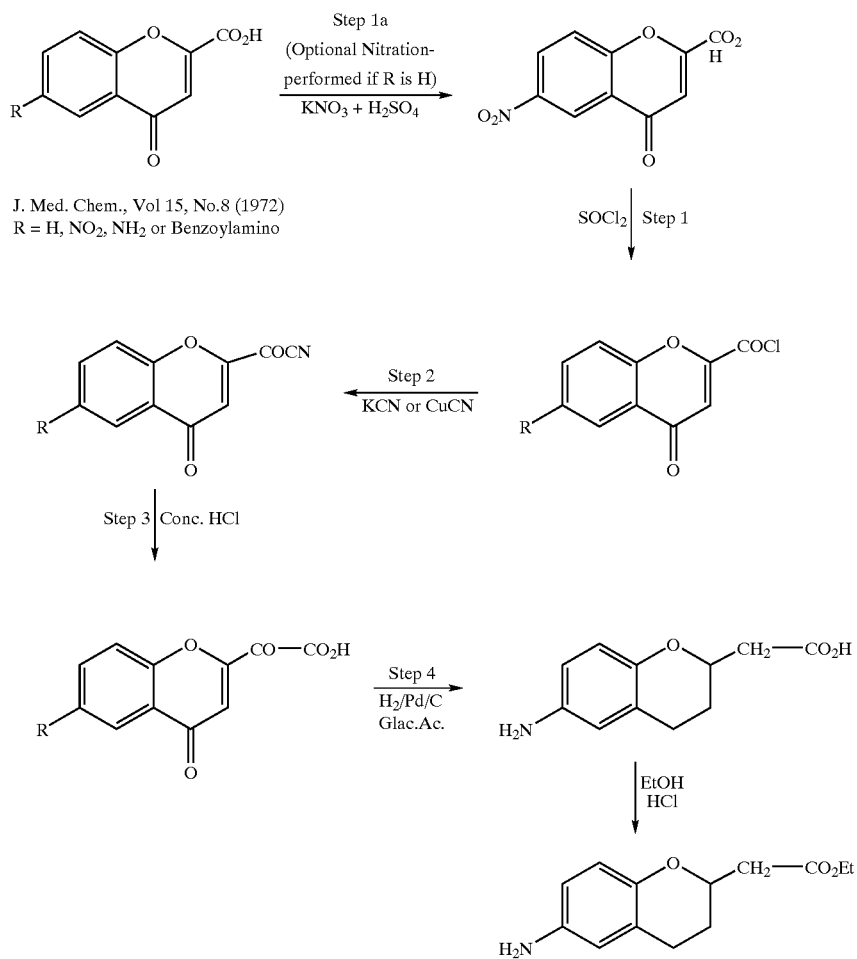
J. Med. Chem., Vol 15, No.8 (1972)
R = H, NO$_2$, NH$_2$ or Benzoylamino
A chiral catalyst could be used in Step 1 to achieve desired stereochemistry at the 2-position.

Scheme III
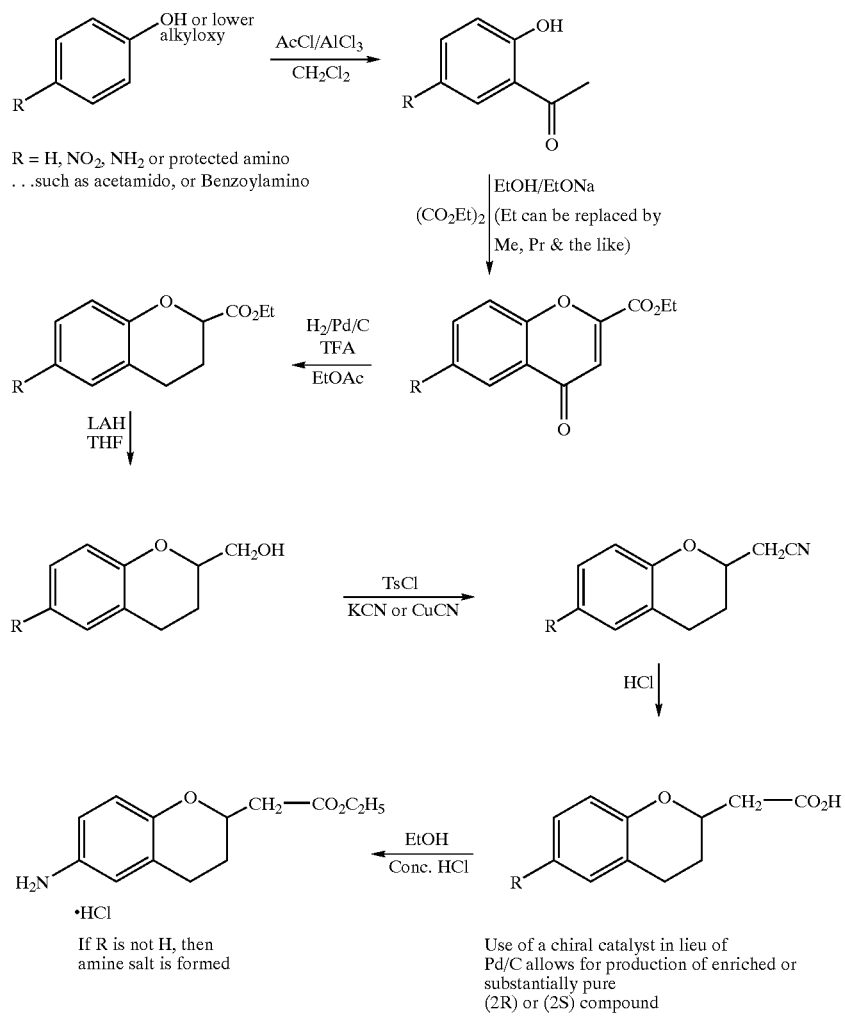
Scheme IV
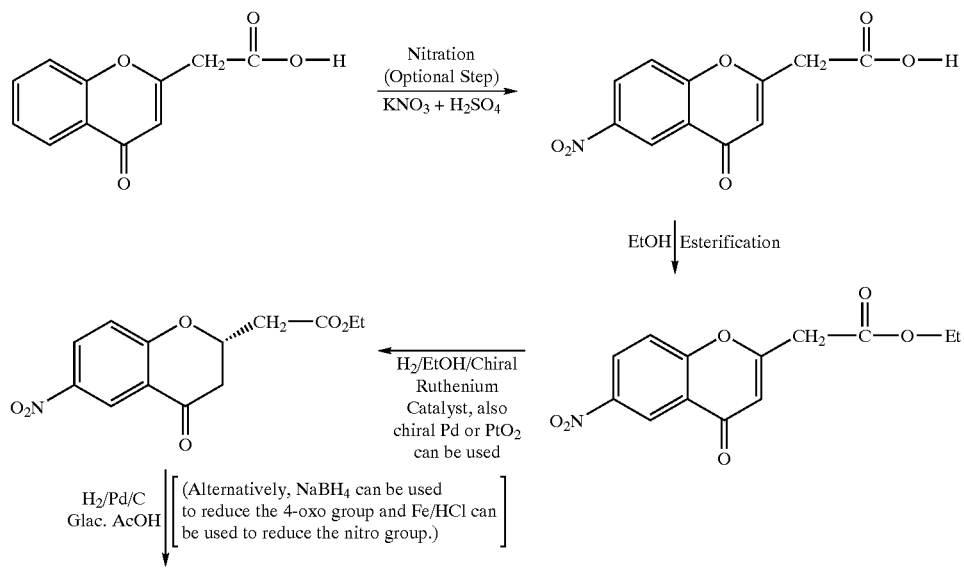

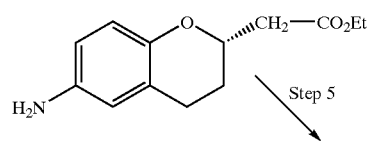
Step 5
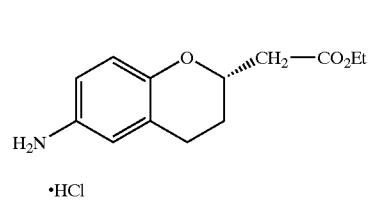
·HCl
Scheme V
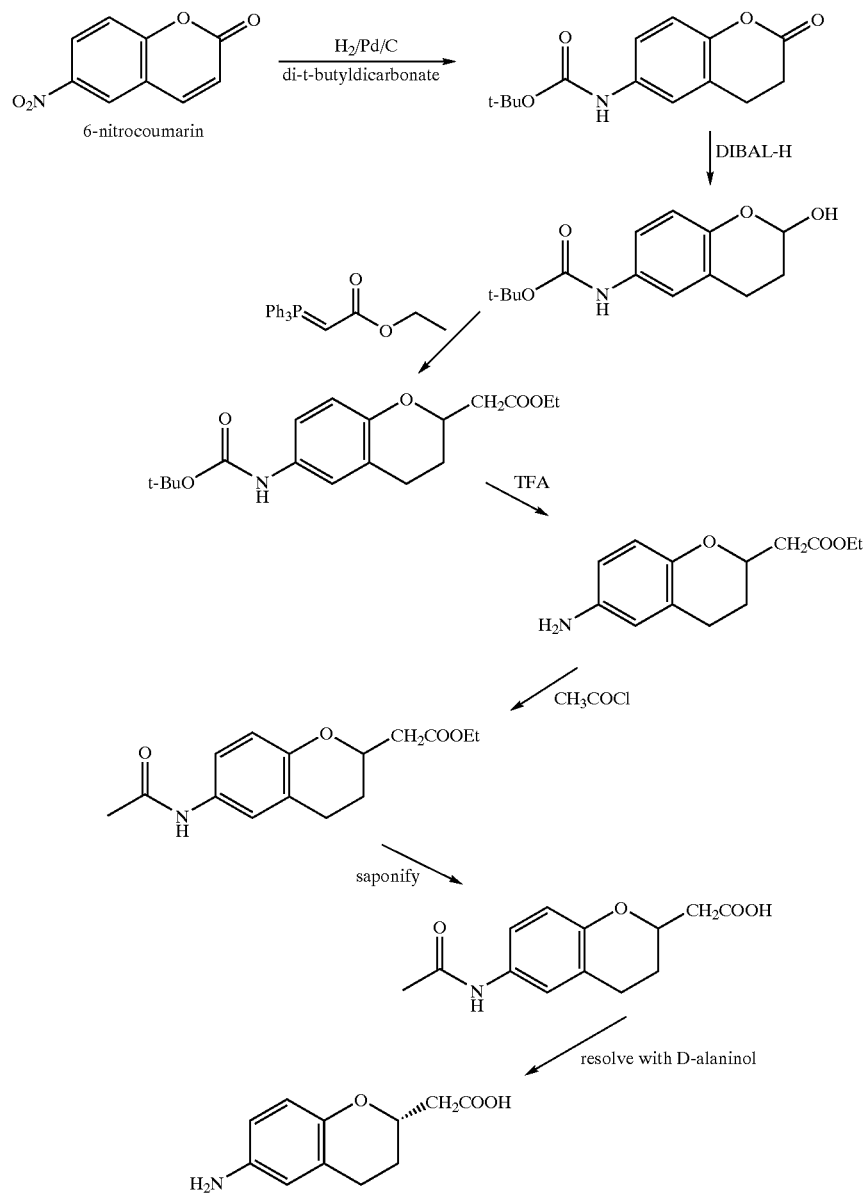

Scheme VI

Examples of Chiral Hydrogenation/Reduction Catalysts

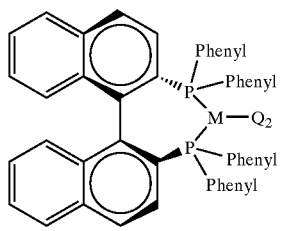

M is a metal atom such as Pd, Pt, Rh, and the like, preferably Pt

Q in each case is independently selected from oxygen and halogen, preferably when M is Pt, each Q is O, when M is Pd or Rh, each Q is Cl In the schemes shown above, the order of some of the reactions may be reversed, some (e.g. chain extension and nitration) some reactions may be omitted (e.g. a final esterification or salt formation step), and reactions from other schemes may be substituted in for other reactions having similar results. Additionally, other reagents and conditions having similar results may be substituted for those disclosed. For reactions producing racemates, resolution of a racemate may occur at any suitable place in the scheme and may proceed with reagents other than lipase, a preferred reagent and process disclosed herein. Furthermore, salts and esters may be formed and/or interconverted with the corresponding free acid or base as desired at any place in the scheme if desired, such as to aid in isolation or purification of a compound or intermediate.

In other embodiments, the order of some of the reactions in the schemes may be changed, and additional steps of protecting, deprotecting, nitrating, hydrolyzing, esterifying, and the like may be added to the schemes at various points. Such minor alterations are within the scope of the disclosure herein. Although the esters shown are primarily ethyl esters, other esters may be made, either by use of different solvents and/or reagents in the initial formation reactions or by transesterification.

The starting materials used in the disclosed processes are commercially available from chemical vendors such as Aldrich, Lancaster, TCI, Bachem Biosciences, and the like, or may be readily synthesized by known procedures including those present in the chemical literature, or may be made by using procedures such as indicated above.

Reactions are carried out in standard laboratory glassware and reaction vessels under reaction conditions of standard temperature and pressure, except where it is otherwise indicated, or where use of non-STP conditions for a procedure is known in the art. Some procedures, reactions, and/or workups which are well known in the art or which are readily available in standard reference texts in the art, including Beilstein and Fieser and Fieser, may not be presented herein owing to their stature of being within the knowledge of one of ordinary skill. Further, the above procedures of the processes may be carried out on a commercial scale by utilizing reactors and standard scale-up equipment available in the art for producing large amounts of compounds in the commercial environment. Such equipment and scale-up procedures are known to the ordinary practitioner in the field of commercial chemical production.

During the synthesis of these compounds, amino or acid functional groups may be protected by blocking groups to prevent undesired reactions with the amino group during certain procedures. Procedures for such protection and removal of protecting groups are routine and well known to the ordinary practitioner in this field.

Enantiomeric Resolution and Acid Salt Formation

When a reaction results in the production of racemic chroman-2-yl carboxylic acids and esters, these racemates are preferably resolved to produce a mixture enriched in one of the R or S enantiomers or completely resolved into a substantially pure composition of one of the enantiomers. Examples of processes for resolving the racemic mixtures are provided herein and/or are known to those skilled in the art. Additionally, processes for the formation of acid addition salts such as the hydrochloride salt of the 6-position amino acid group on the chromane nucleus are known in the art. Other such salts are also envisioned.

Uses of Compounds

As mentioned above, the compounds produced according to preferred embodiments find utility as intermediates for producing therapeutic agents or as therapeutic agents for disease states in mammals, including those which have disorders that are due to platelet dependent narrowing of the blood vessels, such as atherosclerosis and arteriosclerosis, acute myocardial infarction, chronic stable angina, unstable angina, transient ischemic attacks and strokes, peripheral vascular disease, arterial thrombosis, preeclampsia, embolism, restenosis following angioplasty, carotid endarterectomy, anastomosis of vascular grafts, and etc. These conditions represent a variety of disorders thought to be initiated by platelet activation on vessel walls.

Platelet adhesion and aggregation is believed to be an important part of thrombus formation. This activity is mediated by a number of platelet adhesive glycoproteins. The binding sites for fibrinogen, fibronectin and other clotting factors have been located on the platelet membrane glycoprotein complex IIb/IIIa. When a platelet is activated by an agonist such as thrombin, the GP IIb/IIIa binding site becomes available to fibrinogen, eventually resulting in platelet aggregation and clot formation. Thus, intermediate compounds for producing compounds that effective in the inhibition of platelet aggregation and reduction of the incidence of clot formation are useful intermediate compounds.

The compounds produced according to preferred embodiments may also be used as intermediates to form compounds that may be administered in combination or concert with other therapeutic or diagnostic agents. In certain preferred embodiments, the compounds produced by the intermediates according to the present invention may be co-administered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds produced from the intermediates may act in a synergistic fashion to prevent reocclusion following a successful thrombolytic therapy and/or reduce the time to reperfusion. Such compounds may also allow for reduced doses of the thrombolytic agents to be used and therefore minimize potential hemorrhagic side-effects. Such compounds can be utilized in vivo, ordinarily in mammals such as primates, (e.g. humans), sheep, horses, cattle, pigs, dogs, cats, rats and mice, or in vitro.

Coupling Reaction of the Hydrochloride Salt Intermediate Compounds

The above compounds produced according to preferred methods may be isolated and further reacted to substitute a desired group for one or more of the hydrogen atoms on the amino group by a coupling reaction. Particularly preferred is a coupling reaction of the amino group with an acyl halide compound. For example, compounds such as 5-amidino-thiophen-2-yl carboxylic acid derivatives (or an acyl halide such as the acyl chloride) and 4-amidinobenzoyl chloride may be coupled to ethyl (2S)-(6-aminochroman-2-yl) acetate (or its hydrochloride salt) to form ethyl (2S)-[6-(5-amidino-2-thiophenoyl)amino-chroman-2-yl]acetate and—ethyl (2S)-{6-[(4-amidinophenyl) carbonylamino]chroman-2-yl} acetate, or other similar compounds or their derivatives which are known platelet aggregation inhibitors. For examples of such platelet aggregation inhibitors, see U.S. Pat. No. 5,731,324. The ring portion of the above amidino-aroyl or amidino-heteroaroyl derivatives may be substituted by groups such as methyl, ethyl, fluoro, iodo, bromo, chloro, methoxy, ethoxy, and the like which results in compounds that are known platelet aggregation inhibitors. Standard coupling procedures may be utilized, but procedures utilizing reaction mixtures the compounds, in salt form, are suspended in solvents such as acetonitrile, toluene, or the like, are preferred.

The compound formed from the coupling reaction may be used as either the salt or the free base, and may be readily interconverted between the two forms by using procedures which include those known in the art as well as reacting the compound with one or more molar equivalents of the desired acid or base in a solvent or solvent mixture in which the salt is insoluble, or in a solvent after which the solvent is removed by evaporation, distillation or freeze drying. Alternatively, the free acid or base form of the product may be passed over an ion exchange resin to form the desired salt, or one salt form of the product may be converted to another using the same general process. The free base or salts may be purified by various techniques such as recrystallization in a lower alkanol such as methanol, ethanol, propanol, isopropanol and the like, for example, or a mixture thereof. In preferred embodiments, the compound is recovered as the hydrochloride salt and the recrystallization solvent is a 90/10–10/90 mixture of ethanol and isopropanol. Non-toxic and physiologically compatible salts are preferred, although other types of salts may also be used, such as in the processes of isolation and purification.

Compositions and Formulations

Diagnostic and therapeutic applications of the compounds formed by procedures disclosed herein, including the aforementioned coupling reactions, will typically utilize formulations wherein the compound, or a pharmaceutically acceptable salt, solvate, or prodrug, is combined with one or more adjuvants, excipients, solvents, or carriers. The formulations may exist in forms including, but not limited to tablets, capsules or elixirs for oral administration; suppositories; sterile solutions or suspensions for injectable or parenteral administration; or incorporated into shaped articles. Subjects in need of treatment (typically mammalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations are prepared for storage or administration by mixing the compound, or a pharmaceutically acceptable salt, solvate or prodrug thereof, having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counter ions such as sodium and/or nonionic surfactants such as Tween, Pluronics or polyethyleneglycol.

Dosage formulations to be used for parenteral administration are preferably sterile. Sterility is readily accomplished by filtration through sterile membranes such as 0.2 micron membranes, or by other: conventional methods known to those skilled in the art. Formulations are preferably stored in lyophilized form or as an aqueous solution. The pH of such preparations are preferably between 3 and 11, more preferably from 5 to 9 and most preferably from 7 to 8. It will be understood that use of certain of the foregoing excipients, carriers, or stabilizers will result in the formation of cyclic polypeptide salts. While the preferred route of administration is by injection, other methods of administration are also anticipated such as intravenously (bolus and/or infusion), subcutaneously, intramuscularly, colonically, rectally, nasally or intraperitoneally, employing a variety of dosage forms such as suppositories, implanted pellets or small cylinders, aerosols, oral dosage formulations and topical formulations such as ointments, drops and dermal patches. The compounds are desirably incorporated into shaped articles such as implants which may employ inert materials such as biodegradable polymers or synthetic silicones, for example, Silastic, silicone rubber or other polymers commercially available.

The compounds may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds may also be delivered by the use of antibodies, antibody fragments, growth factors, hormones, or other targeting moieties, to which the compound molecules are coupled. The compounds may also be coupled with suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the platelet aggregation inhibitors may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound and formulation, individual determinations may be made to determine the optimal dosage required. The range of therapeutically effective dosages will naturally be influenced by the route of administration, the therapeutic objectives, and the condition of the patient. For injection by hypodermic needle, it may be assumed the dosage is delivered into the body's fluids. For other routes of administration, the absorption efficiency must be individually determined for each inhibitor by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved.

A typical dosage might range from about 0.001 mg/kg to about 1000 mg/kg, preferably from about 0.01 mg/kg to about 100 mg/kg, and more preferably from about 0.10 mg/kg to about 20 mg/kg. Advantageously, the compounds or formulations may be administered several times daily, in a once daily dose, or in other dosage regimens.

Typically, about 0.5 to 500 mg of a compound or mixture of compounds, as the free acid or base form or as a pharmaceutically acceptable salt or prodrug derivative (including esters), is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are a binder such as acacia, corn starch or gelatin, and excipient such as microcrystalline cellulose, a disintegrating agent like corn starch or alginic acid, a lubricant such as magnesium stearate, a sweetening agent such as sucrose or lactose, or a flavoring agent. When a dosage form is a capsule, in addition to the above materials it may also contain a liquid carrier such as water, saline, a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

The compounds and formulations may be used alone or in combination, or in combination with other therapeutic or diagnostic agents. In certain preferred embodiments, the compounds and/or formulations may be coadministered along with other compounds typically prescribed for these conditions according to generally accepted medical practice, such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds and formulations can be utilized in vivo, ordinarily in mammals such as primates, such as humans, sheep, horses, cattle, pigs, dogs, cats, rats and mice, or in vitro.

The compounds, selected and used as disclosed herein, are believed to be useful for preventing or treating a condition characterized by undesired thrombosis, such as (a) the treatment or prevention of any thrombotically mediated acute coronary syndrome including myocardial infarction, unstable angina, refractory angina, occlusive coronary thrombus occurring post-thrombolytic therapy or post-coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, (d) the treatment or prevention of any coagulopathy including disseminated intravascular coagulation (including the setting of septic shock or other infection, surgery, pregnancy, trauma or malignancy and whether associated with multi-organ failure or not), thrombotic thrombocytopenic purpura, thromboanginitis obliterans, or thrombotic disease associated with heparin induced thrombocytopenia, (e) the treatment or prevention of thrombotic complications associated with extracorporeal circulation (e.g. renal dialysis, cardiopulmonary bypass or other oxygenation procedure, plasmapheresis), (f) the treatment or prevention of thrombotic complications associated with instrumentation (e.g. cardiac or other intravascular catheterization, intra-aortic balloon pump, coronary stent or cardiac valve), and (g) those involved with the fitting of prosthetic devices.

Without further description, it is believed that one of ordinary skill in the art can, using the preceding description and the following illustrative examples, make and utilize the compounds disclosed herein and practice the claimed methods. The following working examples therefore, specifically point out preferred embodiments, and are not to be construed as limiting in any way the remainder of the disclosure.

EXAMPLES

Example 1

Production of 6-(tert-butyloxycarbonylamino)chroman-2-one

An 8-L hydrogenation reactor equipped with a stirrer, temperature probes, and a heating and cooling system was charged under nitrogen with 125 g of 10% palladium on carbon, 300 g of powdered 3 Å molecular sieves, 1050 g of 6-nitrocoumarin, 1318 g of di-tert-butyldicarbonate, and 4.0 L of anhydrous tetrahydrofuran. The reactor was purged 5 times with nitrogen and then 5 times with hydrogen. The pressure of hydrogen was maintained at 30 psi until the end of the exotherm (30° C.<T<50° C.), then the reactor was heated to about 50° C., and the hydrogen pressure increased to 60 psi. The reaction was complete in about 15 h by TLC. The reaction mixture was cooled to room temperature and purged 3 times with nitrogen before it was discharged from the reactor. The catalyst and molecular sieves were removed by filtration through Celite and the filter cake was washed with 1.0 L of tetrahydrofuran. The filtrate was concentrated to dryness at 50° C. under reduced pressure to give an off-white crude product. Recrystallization from 3.6 L of toluene afforded 1300 g of 6-(tert-butyloxycarbonylamino) chroman-2-one. The mother liquor was concentrated to afford an additional 47 g of the product (93.1% overall yield).

Example 2
Production of 6-(tert-butyloxycarbonylamino)chroman-2-ol

A 22-L three-neck round-bottom flask equipped with an overhead stirrer and an addition funnel was charged under nitrogen with 7 L of anhydrous methylene chloride and 800 g of 6-(tert-butyloxycarbonylamino)chroman-2-one (Example 1). The solution was cooled to about −55° C., and 2.66 L of diisobutylaluminum hydride (1.58 M solution in toluene, 4.2 mol) was slowly added through the addition funnel to the well-stirred solution. The addition rate was adjusted to keep the temperature of the reaction was between −50° C. and −65° C. requiring about 1.5 h overall. After an additional 1 h stirring, the reaction was complete by TLC. Methanol (870 mL) of was slowly added, keeping the temperature below −50° C. The reaction mixture was warmed up to about −20° C., and 790 g of Celite and 970 mL of water were added. The mixture was warmed to room temperature and stirred vigorously for 40 minutes. The mixture was filtered and the filter cake washed with 10.0 L of methylene chloride. The filtrate and the washings were combined and the solvent removed under reduced pressure at 50° C. The residue was transferred with 8.0 L of toluene into a 22-L three-neck round-bottom flask and dried azeotropically by distilling off 6 L of toluene under reduced pressure at 50° C. The volume of the remaining solution was adjusted to about 8 L with anhydrous toluene to provide a toluene solution of 6-(tert-butyloxycarbonylamino) chroman-2-ol.

Example 3
Production of Ethyl 2-(6-(tert-butyloxycarbonylamino) chroman-2-yl)acetate Into the 6-(tert-butyloxycarbonylamino)chroman-2-ol toluene solution of Example 2 (8 L) was added 1225 g of (carbethoxymethylene)triphenylphosphorane (95%) and 1.1 g of sodium ethoxide. The stirred reaction was heated to 80° C. for 2 h. An additional 3.2 g of sodium ethoxide was added, and the mixture stirred at 80° C. for 18 h. Because the reaction was not complete by TLC, an additional 122 g of (carbethoxymethylene)triphenylphosphorane and 1.0 g of sodium ethoxide was added. The reaction mixture was stirred at 80° C. for 3 h after the addition. The reaction was cooled to room temperature, and 3750 g of silica gel and 7 L of toluene were added. The mixture was stirred for 2 h, filtered, and the filter cake was washed with 2×12 L of toluene. The filtrate and washings were combined, and the volume reduced to about 7 L by distillation under reduced pressure (T≦60° C.) to provide a toluene solution of ethyl 2-(6-(tert-butyloxycarbonylamino)chroman-2-yl)acetate.

Example 4
Production of Ethyl 2-(6-aminochroman-2-yl)acetate

Into the ethyl 2-(6-(tert-butyloxycarbonylamino) chroman-2-yl)acetate toluene solution of Example 3 (7 L) was added 1480 g of trifluoroacetic acid. The solution was warmed to 60° C. for 2 h. After distilling-off about 2 L of toluene under reduced pressure (T≦60° C.), the mixture was cooled to room temperature. About 10 L of 10% (w/w) of aqueous sodium bicarbonate was added slowly to the well-stirred mixture until the pH was above 7. The mixture was stirred for 20 min and the aqueous fraction separated. The aqueous fraction was extracted with 3×1 L of toluene. The combined organic fractions were washed with 3 L of brine, dried over 200 g of anhydrous sodium sulfate, and filtered. The volume of solvent was reduced to 6 L by distillation under reduced pressure (T≦60° C.) to provide a toluene solution of ethyl 2-(6-aminochroman-2-yl)acetate.

Example 5
Production of ethyl 2-(6-acetamidochroman-2-yl)acetate

The ethyl 2-(6-aminochroman-2-yl)acetate toluene solution of Example 4 (6 L) was cooled to −5° C. in a sodium chloride-ice bath, and 293 g of anhydrous pyridine added in a single portion. To the well-stirred mixture was added dropwise 246 g of acetyl chloride, maintaining the temperature between −5° C. and 5° C. The reaction was not complete by TLC after 30 min, so an additional 50 g of anhydrous pyridine and 50 g of acetyl chloride were added dropwise, and the reaction stirred for 30 min. The reaction was quenched with 4 L of water, stirred for 15 minutes, and the organic fraction was separated. The aqueous fraction was extracted with 2×500 mL of toluene, and the combined toluene fractions washed with 2 L of water. Complete removal of toluene afforded ethyl 2-(6-acetamidochroman-2-yl)acetate as a dark brown residue, which was transferred into a 12-L flask.

Example 6
Production of 2-(6-acetamidochroman-2-yl)acetic acid by saponification To the dark brown ethyl 6-acetamidochroman-2-ylacetate of Example 5 was added 3.5 L of methanol and 3.5 L of 1 N aqueous sodium hydroxide. After stirring the reaction mixture for 2 h at room temperature, the methanol was removed from the reaction mixture providing a dark, aqueous residue. The residue was transferred into a separatory funnel and extracted with 3×2 L of methylene chloride. Between each extraction step, the aqueous fraction was distilled to remove any organic solvent. The pH of the aqueous fraction was adjusted to about 2 with 2 N hydrochloric acid, affording a sticky, dark oil, which was separated. The acidic, aqueous fraction was extracted with 3×2 L of ethyl acetate. The ethyl acetate extracts and the dark oil were combined to form a homogenous solution. This solution was washed 2×2 L of brine and dried over 100 g of anhydrous sodium sulfate. Removing the ethyl acetate afforded a thick, blackish oil, which solidified overnight under vacuum. The dark brown solid was dissolved in saturated aqueous sodium bicarbonate to provide a black solution. The well-stirred, black solution was titrated with 3 N hydrochloric acid. At about pH 7.5, a black oil began to form on the walls of the flask. At about pH 7.0, more black oil formed, and the color of the solution changed from black to light yellow. The mixture was allowed to stand for about 5 min for the black oil to settle. The supernatant was decanted and acidified to about pH 2.0. The resulting white suspension was stirred for 30 min. The precipitate was filtered and dried at 50° C. under reduced pressure affording 350 g of 2-(6-acetamidochroman-2-yl)acetic acid as off-white crystals. The overall yield from 1347 g of 6-(tert-butyloxycarbonylamino)chroman-2-one from example 1 was 46.2%.

Example 7
Production of (2S)-(6-acetamidochroman-2-yl)acetic acid, D-alaninol salt A 5-L three-neck round-bottom flask equipped with a condenser and magnetic stirrer was charged with 1.9 L of anhydrous methanol and 240 g of 2-(6-acetamidochroman-2-yl)acetic acid (Example 8). The solution was heated to reflux, 39.8 g of D-alaninol was added in a single portion, and the reaction mixture was refluxed for 15 min. The solution was cooled to 45° C. and stirred for about 30 min. The solution was seeded with about 50 mg of (2S)-(6-acetamidochroman-2-yl)acetic acid, D-alaninol salt crystals. The solution became turbid after about 5 min, then a large amount of white crystals formed. The suspension was slowly cooled and the stirring continued at room temperature for 14 h. The crystals were filtered, washed with 200 mL of methanol, and dried to afford 135 g of (2S)-(6-acetamidochroman-2-yl)acetic acid, D-alaninol salt (43.2% crude yield). The crude crystals were suspended in 2.0 L of methanol and heated at reflux for 8 h. The suspension was slowly cooled and allowed to stand at room temperature for a few h. The crystals were filtered, rinsed with 15 mL of methanol, and dried to give 122 g (39.1% yield) of (2S)-(6-acetamidochroman-2-yl)Acetic Acid, D-alaninol salt.

Example 8
Production of ethyl (2S)-(6-aminochroman-2-yl)acetic acid, bisulfate salt A 3-L three-neck round-bottom flask equipped with a condenser and an addition funnel was charged with 900 mL of absolute ethanol and 97.3 g of (2S)-(6-acetamidochroman-2-yl)acetic acid, D-alaninol salt (example 7). To this well-stirred mixture was slowly added 92 mL of concentrated sulfuric acid through the addition funnel. The solution was refluxed for 18 h, then cooled to room temperature. The cooled mixture was slowly poured into a well-stirred mixture of 150 g of sodium bicarbonate, 800 g of ice, 600 mL of water, and 1.0 L of methylene chloride. The mixture was stirred 20 min, and the aqueous fraction separated and extracted with 400 mL of methylene chloride. The combined organic fractions were washed with 600 mL of brine and concentrated to a brown residue. The residue was dissolved in 1.0 L of toluene, and the volume reduced to 500 mL by distillation to provide ethyl (2S)-(6-aminochroman-2-yl)acetic acid, bisulfate salt as a toluene solution.

Example 9
Production of ethyl (2S)-(6-aminochroman-2-yl)acetic acid, hydrochloride salt A 2-L three-neck round-bottom flask equipped with a condenser and a stirrer was charged with ethyl (2S)-(6-aminochroman-2-yl)acetic acid, bisulfate salt in 500 mL of toluene (Example 8). The reaction was cooled to about 10° C., and 55 mL of 5.8 M hydrochloric acid in absolute ethanol was added to the well-stirred solution. The resulting suspension was stirred for 17 h, then the crystals were allowed to settle. The white crystals were filtered, washed with 250 mL of toluene, and dried at 60° C. under reduced pressure to afford 75 g of ethyl (2S)-(6-aminochroman-2-yl)acetic acid, hydrochloride salt (92% with respect to (2S)-(6-acetamidochroman-2-yl)acetic acid, D-alaninol salt from Example 7). The product was >99% pure and the enantiomeric excess was >99.5% by chromatography and NMR.

Example 10
Production of ethyl 6-nitrochromone-2-carboxylate

Into a solution of 12.0 g of diethyl oxalate in 180 g of toluene is added 28 g of 5-nitro-2-hydroxyacetophenone, then dropwise added 62.0 g of 20% sodium ethoxide in ethanol. After the reaction is complete, 12.6 g of 98% sulfuric acid is added, and the mixture stirred at 60° C. for about 30 min. After adding 140 g of water, the organic fraction is separated. The organic fraction is concentrated and 54.0 g of hexane is added. Filtering below 10° C. affords about 33.0 g of ethyl 6-nitrochromone-2-carboxylate (about 95% yield).

Example 11
Production of ethyl 6benzamidochromone-2-carboxylate

Into a solution of 12.0 g of diethyl oxalate in 180 g of toluene is added 30 g of 5-benzamido-2-hydroxyacetophenone, then dropwise added 65.0 g of 20% sodium ethoxide in ethanol. After the reaction is complete, 12.6 g of 98% sulfuric acid is added, and the mixture stirred at 60° C. for about 30 min. After adding 140 g of water, the organic fraction is separated. The organic fraction is concentrated and 54.0 g of hexane is added. Filtering below 10° C. affords about 36.5 g of ethyl 6-benzamidochromone-2-carboxylate (about 96% yield).

Example 12
Production of ethyl 6-acetamidochromane-2-carboxylate

A hydrogenation apparatus is charged with 6 g of ethyl 6-nitrochromone-2-carboxylate (Example 10), 3.5 mL of acetic anhydride, 1 g of 10% palladium on carbon, 4.0 g of dry, powdered 3A molecular sieves, and 30 mL of glacial acetic acid. After purging several times with nitrogen, the apparatus is purged several times with hydrogen. Under continuous stirring, the apparatus is maintained at about 70 psi with hydrogen and about 80° C. for about 10–12 h. The apparatus is then cooled to about 50° C., evacuated of hydrogen, and purged several times with nitrogen. Trifluoroacetic acid (3.5 mL) is added to the mixture, then the apparatus is resealed, purged several times with hydrogen, and pressurized to 70 psi with hydrogen. The stirred reaction mixture is heated to 80° C. until the reaction is complete by HPLC (intermediate:product$\leqq$3%), then cooled to room temperature. After filtering the mixture through Celite, the catalyst and molecular sieves are washed with 10 mL aliquots of glacial acetic acid, and the washes combined with the filtrate. These combined filtrates are concentrated by mild distillation to an oil, which is dissolved in ethyl acetate and washed with saturated $NaHCO_3$. The aqueous fraction is extracted with ethyl acetate, then made strongly acidic with concentrated HCl and extracted several times with ethyl acetate. The combined ethyl acetate fractions are combined and concentrated to a solid. The solid is washed with acetonitrile, filtered, and dried to afford about 3.5–4.0 g of ethyl 6-acetamidochromane-2-carboxylate as a white solid.

Example 13
Production of 6-acetamido-2-hydroxymethylchromane

To a solution of 3.0 grams of ethyl 6-acetamidochromane-2-carboxylate (Example 12) dissolved in 20 mL of dry ether is added dropwise a solution of 1 mL of lithium aluminum hydride (70% in benzene) dissolved in about 2 mL of dry ether, and the solution is refluxed for about 1 h. An additional 1 mL of lithium aluminum hydride is added to the mixture, and the mixture refluxed for an additional 1–2 h. The reaction mixture is cooled to 0° C. and the excess hydride quenched by adding 10–12 mL of 1 N $H_2SO_4$, followed by 100 mL of water. The precipitate is filtered and washed well with ether. The aqueous phase is separated, extracted several times with 60-mL aliquots of ether. The combined extracts are washed with water and dried over anhydrous $MgSO_4$. Evaporation to dryness under vacuum affords about 2.4 g of 6-acetamido-2-hydroxymethylchromane (about 90% yield).

Example 14
Production of 6-acetamido-2-cyanomethylchromane

To a solution of 2.0 g of 6-acetamido-2-hydroxymethylchromane (Example 13) in 35 mL of $CH_2Cl_2$ and 1.5 mL of pyridine is added 2 g p-toluenesulfonyl chloride. The mixture is stirred at 25° C. for 36 h, then diluted with 20 mL ether, and washed with 10 mL. The organic layer is dried over $MgSO_4$ and concentrated to give 3.4 grams of the tosylate. To a stirred solution of the tosylate in 20 mL of DMSO is added 80 mg of powdered sodium cyanide. The mixture refluxed for 1.5 h under an inert atmosphere, then cooled, diluted with 50 mL of water, and extracted 6×100 mL portions of ether. The combined ether extracts are dried over anhydrous $MgSO_4$ and filtered. The filtrate is concentrated and the residue is recrystallized from ether/isopropanol to afford 1.7 grams of 6-acetamido-2-cyanomethylchromane (about 85% yield).

Example 15

Production of ethyl 2-(6-aminochroman-2-yl)acetate hydrochloride

A mixture of 1.5 g of 6-acetamido-2-cyanomethylchromane (Example 14) in 25 mL of concentrated hydrochloric acid is stirred vigorously at room temperature for about 6 h. Ethanol (50 mL) is added and the mixture allowed to stand overnight. The precipitate is filtered, rinsed with 50-mL aliquots of ether, and dried. Absolute ethanol (25 mL) and HCl (10 mL) are stirred with the precipitate for 2 h, followed by addition of 10 mL of concentrated HCl. The precipitate is recovered and recrystallized twice from ether/isopropanol affording about 1.3 g of ethyl 2-(6-aminochroman-2-yl)acetate hydrochloride (about 80% yield).

Example 16

Production of ethyl chromone-2-carboxylate

Into a solution of 12.0 g of diethyl oxalate in 180 g of toluene is added 30 g of 2-hydroxyacetophenone, then dropwise added 65.0 g of 20% sodium ethoxide in ethanol. After the reaction is complete, 13 g of 98% sulfuric acid is added, and the mixture stirred at 60° C. for about 30 min. After adding 140 g of water, the organic fraction is separated. The organic fraction is concentrated and 55.0 g of hexane is added. Filtering below 10° C. affords about 34.0 g of ethyl chromone-2-carboxylate (about 95% yield).

Example 17

Production of ethyl 6-nitrochromone-2-carboxylate

To a solution of ethyl chromone-2-carboxylate (Example 16) in about 3 mL of sulfuric acid cooled to −10° C. is added about 1 mL potassium nitrate in sulfuric acid. The molar ratio of potassium nitrate to the benzopyran is slightly greater than 1:1. The reaction mixture is stirred at 0° C. for 1 h, the ice bath removed, and the reaction stirred at room temperature until the reaction is complete by HPLC (<3% benzopyran): about 4–6 h. The nitrated benzopyran precipitates as the reaction progresses. The reaction mixture is poured onto ice, and the precipitate is dissolved in ethyl acetate. The ethyl acetate layer is dried, filtered, and evaporated to afford ethyl 6-nitrochromone-2-carboxylate as a light yellow solid (about 90% yield).

Example 18

Production of 6-amino-2-hydroxymethylchromane

To a stirred solution of 11.4 grams (61.7 mmol) of 6-aminochroman-2-carboxylic acid in 100 mL of THF was slowly added 6.64 g (122 mmol) of lithium aluminum hydride. The mixture was refluxed for 30 min, then quenched with ethyl acetate and 150 mL of 1 N HCl. Sufficient 12 N HCl was added to completely dissolve all of the inorganic precipitates. The aqueous phase was extracted twice with ethyl acetate, and the organic fractions combined, washed twice with brine, and concentrated in vacuo to an oil. This oil was distilled to afford 9.28 g of 6-amino-2-hydroxymethylchromane as a clear oil that crystallizes on cooling (87.6% yield).

The procedures above may be altered to use different starting materials, such as those having different substituents at the 6-position (amino, protected amino, hydrogen, etc.) Additionally, other minor modifications may be done, such as to substitute the diethyl ester of malonic acid for the oxalic acid diester in Examples 10 and 16, and/or to use a non-nitrated ring so as to produce a starting material as in Scheme IV. Chiral catalysts or other reduction/hydration methods may be utilized which allow one to achieve enantiomerically enriched or substantially enantiomerically pure products and intermediates. Furthermore, other alcohols may be used to make other esters, or the esters may be hydrolyzed to provide the free acid.

In view of the above description it is believed that one of ordinary skill can practice the invention. The examples given above are non-limiting in that one of ordinary skill in view of the above will readily envision other permutations and variations on the invention without departing from the principal concepts. Such permutations and variations are also within the scope of the present invention.

What is claimed is:

1. A process for making a compound according to the formula

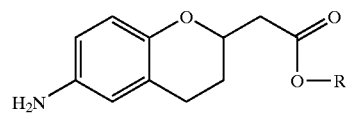

wherein R is H or an alkyl group, comprising:

(a) hydrogenating a compound of the formula:

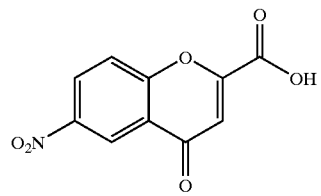

to produce a compound of the formula:

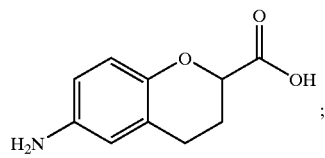

(b) reducing the carboxylic acid of compound of (a) to afford a compound as follows:

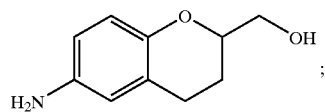

(c) transforming the hydroxyl group of compound of (b) into a leaving group to afford a compound as follows:

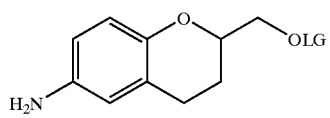

wherein OLG is a leaving group;

(d) reacting the compound of (c) with cyanide ion to afford a compound as follows:

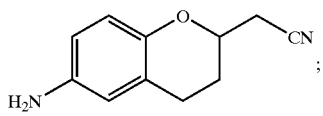

(e) hydrolyzing the compound of (d) to afford a compound as follows:

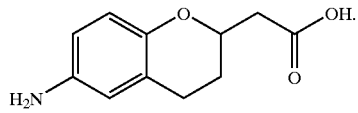

2. The process according to claim 1, wherein the hydrogenation of step a) is performed with $H_2$/Pd/C.

3. The process according to claim 1, wherein the reduction step b) is performed with a chemical reducing agent.

4. The process according to claim 3, wherein the chemical reducing agent is a reagent selected from the group consisting of lithium aluminum hydride, borane, and aluminum hydride.

5. The process according to claim 1, wherein the OLG of step c) is a group selected from the group consisting of tosylate, mesylate, and halogen.

6. The process according to claim 5, wherein the OLG is tosylate.

7. The process according to claim 1, wherein the hydrolysis step e) is performed with heating the compound of step d) in aqueous mineral acid.

8. The process according to claim 7, wherein the mineral acid is hydrochloric acid.

9. The process according to claim 1, further comprising (f) converting the acid group to an ester group, wherein step e) and step f) are performed in one reaction mixture containing reagents comprising a mineral acid and an alcohol.

10. The process according to claim 9, wherein the mineral acid is hydrochloric acid and the alcohol is ethanol.

11. A process for making a compound according to the formula

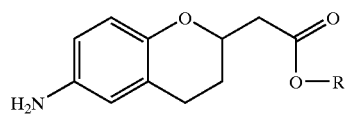

wherein R is H or an alkyl group, comprising:

(a) halogenating a compound of the formula:

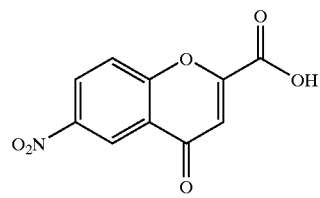

to produce a 2-hydroxy chromane compound of the formula:

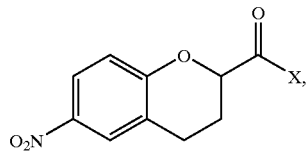

wherein X is a halogen;

(b) reacting the compound of (a) with cyanide ion to afford a compound as follows:

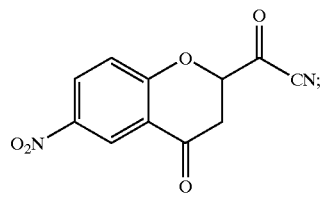

(c) hydrolyzing the compound of (b) to afford a compound as follows:

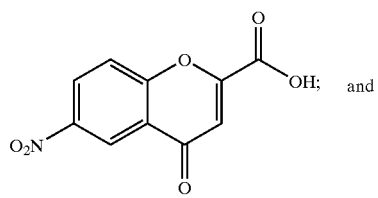

(d) reducing the keto group and nitro groups of compound of (c) by hydrogenation to afford a compound as follows:

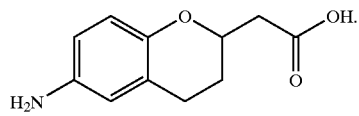

12. The process according to claim 11, wherein the halogenation step (a) is performed with thionyl chloride, thereby producing a compound of the formula:

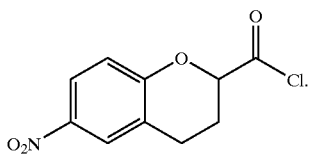

13. The process according to claim 11, wherein the hydrolysis step (c) is performed with heating the compound of step h) in aqueous mineral acid.

14. The process according to claim 13, wherein the mineral acid is hydrochloric acid.

15. The process according to claim 11, wherein the hydrogenation of step (d) is performed with $H_2$/Pd/C.

16. The process according to claim 11, further comprising (e) adding an alkyl group to form an ester, wherein (e) is performed with a mineral acid and an alcohol.

17. The process according to claim 16, wherein the mineral acid is hydrochloric acid and the alcohol is ethanol.

18. A process for making a compound according to the formula

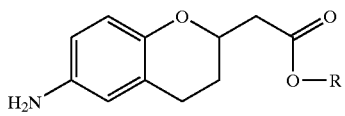

wherein R is H or an alkyl group, comprising:

(a) hydrogenating a compound of the formula and adding a protecting group to a subsequently formed amine:

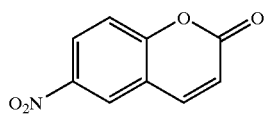

to produce a compound of the formula:

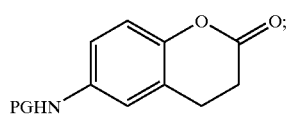

wherein PG is the protecting group;

(b) reducing the ketone of the lactone of compound of (a) to afford a compound as follows:

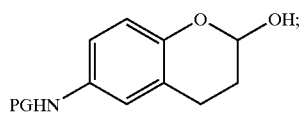

(c) transforming the hydroxyl group of compound of (b) into a carbon chain with a carbon nucleophile to afford a compound as follows:

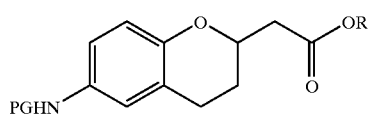

wherein R is an alkyl group;

(d) hydrolyzing the compound of (c) to remove the alkyl group from the ester to afford a compound as follows:

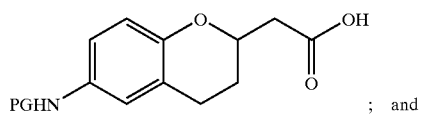

; and (e) removing the protecting group from the amine, thereby obtaining the compound of the formula:

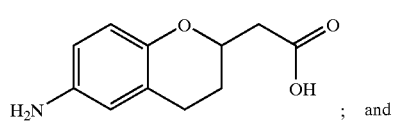

; and

19. The process according to claim 18, wherein the hydrogenation step a) is performed with $H_2$/Pd/C.

20. The process according to claim 18, wherein the reduction step b) is performed with a chemical reducing agent.

21. The process according to claim 20, wherein the chemical reducing agent is DIBAL-H.

22. The process according to claim 18, wherein the carbon nucleophile of step c) is a phosphorus ylide.

23. The process according to claim 22, wherein the phosphorus ylide is (carbethoxymethylene) triphenylphosphine.

24. The process according to claim 18, wherein PG is a group selected from the group consisting of t-BOC and acetyl.

25. The process according to claim 1, for making a compound according to the formula:

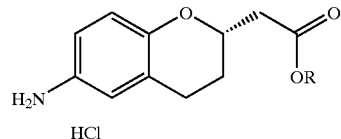

in greater than 95% enantiomeric purity with respect to the corresponding (2R) enantiomer, further comprising:

(i) resolving the racemate; and
(ii) forming the hydrochloride salt of the amine of the resolved compound.

26. The process according to claim 25, wherein the racemate comprises a nitro compound or an amine compound.

27. The process according to claim 25, comprising resolution occurring with an enzyme by an enzymatic cleavage of one enantiomer over the other enantiomer.

28. The process according to claim 25, comprising resolution occurring by hydrolyzing the ester to a carboxylic acid, reacting the carboxylic acid with a chiral reagent to form a salt; and precipitating the salt of one enantiomer, thereby separating one enantiomer over the other enantiomer.

29. A process for making a compound according to the formula

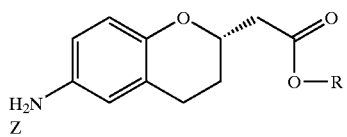

wherein R is an alkyl group and Z is a counterion to the amine salt, further comprising:

(a) hydrogenating the compound of the formula:

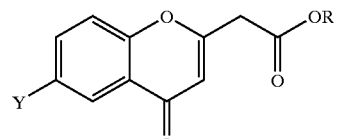

wherein Y is a nitro, amino or protected amino group, with a chiral catalyst to afford a compound as follows:

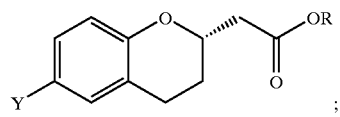

(b) reducing the nitro group of compound of (a) by hydrogenation to afford a compound as follows or removing the amino protecting group to produce a compound of the formula:

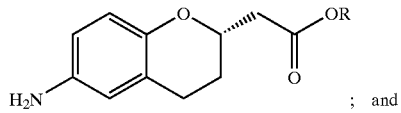
; and (c) forming the amine salt by reaction of compound of (b) with a mineral acid.

30. The process according to claim 29 wherein the chiral catalyst comprises ruthenium, rhodium, palladium or platinum.

31. The process according to claim 29 wherein the chiral catalyst comprises BINAP.

32. The process according to claim 29 wherein the chiral catalyst is a reagent selected from the group consisting of

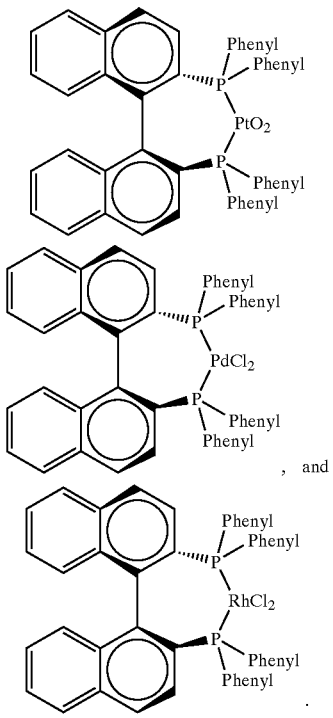

33. The process according to claim 29 wherein the hydrogenation step g) is performed with $H_2$/Pd/C.

34. The process according to claim 29 wherein the mineral acid of step h) is hydrochloric acid.

35. The process according to claim 1, further comprising (f) converting the acid group to an ester group.

36. The process according to claim 11, further comprising
(e) adding an alkyl group to form an ester.

37. The process according to claim 18, further comprising
(f) adding an alkyl group to form an ester.

38. The process according to claim 11, for making a compound according to the formula:

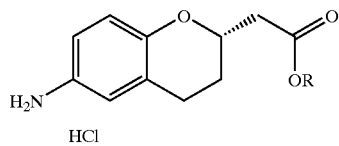

in greater than 95% enantiomeric purity with respect to the corresponding (2R) enantiomer, further comprising:

(i) resolving the racemate; and
(ii) forming the hydrochloride salt of the amine of the resolved compound.

39. The process according to claim 38, wherein the racemate comprises a nitro compound or an amine compound.

40. The process according to claim 38, comprising resolution occurring with an enzyme by an enzymatic cleavage of one enantiomer over the other enantiomer.

41. The process according to claim 38, comprising resolution occurring by hydrolyzing the ester to a carboxylic acid, reacting the carboxylic acid with a chiral reagent to form a salt; and precipitating the salt of one enantiomer; thereby separating one enantiomer over the other enantiomer.

42. The process according to claim 18, for making a compound according to the formula:

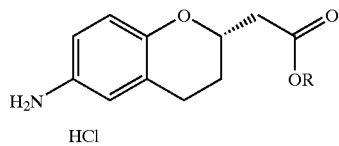

in greater than 95% enantiomeric purity with respect to the corresponding (2R) enantiomer, further comprising:

(i) resolving the racemate; and
(ii) forming the hydrochloride salt of the amine of the resolved compound.

43. The process according to claim 42, wherein the racemate comprises a nitro compound or an amine compound.

44. The process according to claim 42, comprising resolution occurring with an enzyme by an enzymatic cleavage of one enantiomer over the other enantiomer.

45. The process according to claim 42, comprising resolution occurring by hydrolyzing the ester to a carboxylic acid, reacting the carboxylic acid with a chiral reagent to form a salt; and precipitating the salt of one enantiomer; thereby separating one enantiomer over the other enantiomer.

* * * * *

UNITED STATES PATENT AND TRADEMARK OFFICE
CERTIFICATE OF CORRECTION

PATENT NO. : 6,903,227 B2 Page 1 of 1
DATED : June 7, 2005
INVENTOR(S) : James Kanter et al.

It is certified that error appears in the above-identified patent and that said Letters Patent is hereby corrected as shown below:

Column 31,
Line 21, after "claim 1" delete "." and insert -- , --.

Column 32,
Lines 3-10, delete " 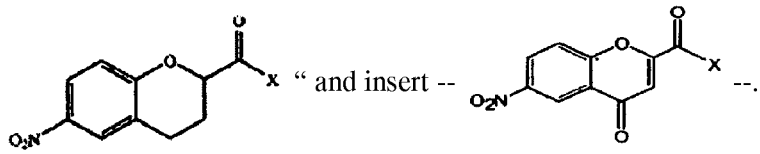 " and insert -- --.

Lines 15-24, delete " 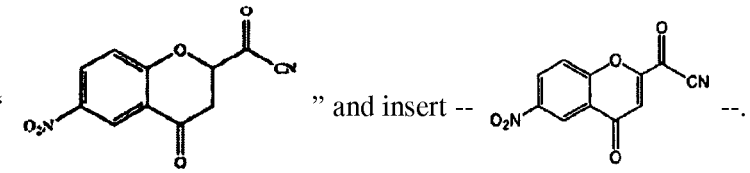 " and insert -- --.

Lines 50-55, delete " 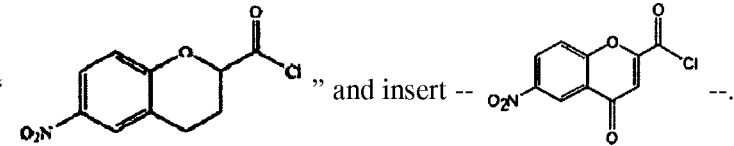 " and insert -- --.

Column 33,
Line 64, after "  " delete "; and" and insert -- . --.

Signed and Sealed this

Seventeenth Day of January, 2006

JON W. DUDAS
*Director of the United States Patent and Trademark Office*